(12) United States Patent
Davis et al.

(10) Patent No.: US 11,813,050 B2
(45) Date of Patent: Nov. 14, 2023

(54) SELECTIVELY SORTING AEROSOL DROPLETS IN EXHALED HUMAN BREATH BASED ON A MASS-SIZE PARAMETER

(71) Applicant: The Regents of the University of California, Oakland, CA (US)

(72) Inventors: Cristina E. Davis, Davis, CA (US); Konstantin O. Zamuruyev, Davis, CA (US); Michael Schivo, Davis, CA (US); Nicholas J. Kenyon, Davis, CA (US); Jean-Pierre Delplanque, Davis, CA (US); Alexander A. Aksenov, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 711 days.

(21) Appl. No.: 16/347,560

(22) PCT Filed: Nov. 22, 2017

(86) PCT No.: PCT/US2017/063018
§ 371 (c)(1),
(2) Date: May 3, 2019

(87) PCT Pub. No.: WO2018/098281
PCT Pub. Date: May 31, 2018

(65) Prior Publication Data
US 2019/0274584 A1 Sep. 12, 2019

Related U.S. Application Data

(60) Provisional application No. 62/425,282, filed on Nov. 22, 2016.

(51) Int. Cl.
*A61B 5/097* (2006.01)
*A61B 5/08* (2006.01)
(Continued)

(52) U.S. Cl.
CPC .............. *A61B 5/082* (2013.01); *A61B 5/097* (2013.01); *A61M 16/0808* (2013.01);
(Continued)

(58) Field of Classification Search
CPC .... A61B 5/082; A61B 5/097; A61M 16/0808; A61M 15/00; G01N 15/0255; G01N 33/497; G01N 2015/0288
See application file for complete search history.

(56) References Cited

U.S. PATENT DOCUMENTS 8,176,766 B1 * 5/2012 Ruiz .................... G01N 1/2211
73/23.3
2003/0105407 A1 * 6/2003 Pearce, Jr. ............. A61B 5/097
600/532
(Continued)

FOREIGN PATENT DOCUMENTS

KR  20120000705 A  *  1/2012  ............. G01N 15/02
WO  20130112893 A1    8/2013

OTHER PUBLICATIONS

An English-language machine translation of KR-20120000705-A (Year: 2021).*
(Continued)

*Primary Examiner* — Andrey Shostak
(74) *Attorney, Agent, or Firm* — Park, Vaughan, Fleming & Dowler LLP (57) ABSTRACT

A selective-sorting system for aerosol droplets in human breath includes a mouthpiece to receive a flow of human breath, and a flow path coupled to the mouthpiece. This flow path includes one or more bends that cause the flow of human breath to change direction, which causes aerosol droplets in the flow having different mass-sizes to change direction at different rates. Moreover, the flow path is shaped so that droplets that change direction at different rates are directed to different destinations. The system also includes a
(Continued)

collection path, which is coupled to the flow path so that aerosol droplets meeting a specific mass-size criterion are directed into the collection path. A condenser tube is located in the collection path, wherein the condenser tube includes a cooling mechanism that cools the condenser tube to facilitate condensing aerosol droplets to sides of the condenser tube for subsequent collection.

18 Claims, 8 Drawing Sheets
(2 of 8 Drawing Sheet(s) Filed in Color)

(51) Int. Cl.
  *G01N 15/02* (2006.01)
  *G01N 33/497* (2006.01)
  *A61M 16/08* (2006.01)
  *A61M 15/00* (2006.01)

(52) U.S. Cl.
  CPC ....... *G01N 15/0255* (2013.01); *G01N 33/497* (2013.01); *A61M 15/00* (2013.01); *G01N 2015/0288* (2013.01)

(56) References Cited

U.S. PATENT DOCUMENTS

| | | | |
|---|---|---|---|
| 2004/0112380 A1* | 6/2004 | Djupesland | A61B 5/415 128/203.12 |
| 2004/0176698 A1* | 9/2004 | Robergs | A61B 5/083 600/531 |
| 2010/0297635 A1* | 11/2010 | Olin | A61B 5/411 435/6.11 |
| 2011/0270541 A1* | 11/2011 | Cha | G01F 1/36 702/47 |
| 2013/0190639 A1* | 7/2013 | Kline | G01N 33/92 600/532 |
| 2013/0303929 A1* | 11/2013 | Martino | A61B 5/082 600/532 |
| 2014/0288454 A1* | 9/2014 | Paz | A61B 5/4845 600/532 |
| 2015/0033824 A1* | 2/2015 | Hammarlund | A61B 5/097 73/23.3 |
| 2015/0122261 A1* | 5/2015 | Pettitt | A61M 16/049 128/205.24 |
| 2016/0000358 A1 | 1/2016 | Lundin et al. | |
| 2017/0196481 A1* | 7/2017 | Rundell | A61B 5/082 |

OTHER PUBLICATIONS

International Search Report and Written Opinion PCT/US2017/63018, dated Feb. 5, 2018, Authorized Officer Shane Thomas.

Aksenov, et al. "Metabolite Content Profiling of Bottlenose Dolphin Exhaled Breath", Anal. Chem. Sep. 25, 2014, vol. 86, pp. 10616-10624, dx.doi.org/10.1021/ac5024217.

* cited by examiner

```
                          ┌─────────┐
                          │  START  │
                          └────┬────┘
                               ▼
┌──────────────────────────────────────────────────────────────┐
│   RECEIVE A FLOW OF HUMAN BREATH THROUGH A                   │
│                    MOUTHPIECE                                │
│                        302                                   │
└──────────────────────────────┬───────────────────────────────┘
                               ▼
┌──────────────────────────────────────────────────────────────┐
│  CHANNEL THE RECEIVED FLOW OF HUMAN BREATH                   │
│  THROUGH A FLOW PATH, WHEREIN THE FLOW PATH                  │
│  INCLUDES ONE OR MORE BENDS, BENDED CURVES, OR               │
│  CURVES WITH ENLARGING OR REDUCING DIAMETERS,                │
│  THAT CAUSE THE FLOW OF HUMAN BREATH TO CHANGE               │
│  DIRECTION, THEREBY CAUSING AEROSOL DROPLETS IN              │
│  THE FLOW HAVING DIFFERENT MASS-SIZES TO CHANGE              │
│     DIRECTION AT DIFFERENT RATES BECAUSE OF                  │
│  DIFFERENCES IN MOMENTUM FOR DIFFERENT DROPLET               │
│     MASSES, AND DIFFERENCES IN AIR-FLOW-RELATED              │
│   FRICTIONAL FORCES FOR DIFFERENT DROPLET SIZES,             │
│    AND WHEREIN THE FLOW PATH IS SHAPED SO THAT               │
│    DROPLETS THAT CHANGE DIRECTION AT DIFFERENT               │
│   RATES ARE DIRECTED TO DIFFERENT DESTINATIONS               │
│                        304                                   │
└──────────────────────────────┬───────────────────────────────┘
                               ▼
┌──────────────────────────────────────────────────────────────┐
│   RECEIVE A SUBSET OF THE AEROSOL DROPLETS THAT              │
│    MEET A SPECIFIC MASS-SIZE CRITERION IN A                  │
│   COLLECTION PATH, WHICH IS COUPLED TO THE FLOW              │
│                        PATH                                  │
│                        306                                   │
└──────────────────────────────┬───────────────────────────────┘
                               ▼
┌──────────────────────────────────────────────────────────────┐
│  CHANNEL THE SUBSET OF AEROSOL DROPLETS FROM                 │
│  THE COLLECTION PATH THROUGH A CONDENSER TUBE                │
│                        308                                   │
└──────────────────────────────┬───────────────────────────────┘
                               ▼
┌──────────────────────────────────────────────────────────────┐
│   COOL THE CONDENSER TUBE TO CAUSE THE SUBSET OF             │
│   AEROSOL DROPLETS TO CONDENSE ON SIDES OF THE               │
│   CONDENSER TUBE FOR SUBSEQUENT COLLECTION                   │
│                        310                                   │
└──────────────────────────────┬───────────────────────────────┘
                               ▼
                          ┌─────────┐
                          │  STOP   │
                          └─────────┘
```

SELECTIVELY SORTING AEROSOL DROPLETS IN EXHALED HUMAN BREATH BASED ON A MASS-SIZE PARAMETER

CROSS-REFERENCE TO RELATED APPLICATION

This application claims the benefit of U.S. Provisional Patent Application Ser. No. 62/425,282, entitled "Apparatus for Selective Sorting of Aerosol Droplets Based on a Mass-Diameter Parameter from an Aerosol Flow," by inventors Cristina E. Davis, filed on 22 Nov. 2016, the contents of which are incorporated by reference herein.

BACKGROUND

Field

The disclosed embodiments generally relate to techniques for analyzing exhaled human breath. More specifically, the disclosed embodiments relate to an aerodynamic technique for selectively sorting aerosol droplets in exhaled human breath based on a mass-size threshold.

Related Art

Exhaled breath analysis is a developing field with tremendous promise to facilitate personalized, non-invasive health diagnostic techniques. Exhaled breath contains potentially valuable metabolomic content due to gas exchange with blood at the pulmonary alveolar membrane interface. Empirical results show that a number of biomarkers in exhaled breath and exhaled breath condensate (EBC) are highly correlated with those in other biological fluids such as blood and urine, which are routinely used for health diagnostics. Due to the completely non-invasive nature of breath analysis, it offers a safe technique for assessing health in children with inflammatory diseases such as asthma, patients with acute cardiovascular or pulmonary diseases, and for unresponsive patients receiving respiratory ventilator assistance.

In designing a human breath sampler (HBS), the efficiency of the passage of aerosolized microdroplets from the breath flow through the sampler is an important design factor. Exhaled breath comprises a complex mixture of gasses, such as nitrogen, oxygen, $CO_2$, inert gases, and hundreds of volatile organic compounds (VOCs) of exogenous and endogenous origin in trace concentrations, along with water vapor and non-volatile compounds contained in microdroplets.

The origin of the droplets exhaled with breath determines their metabolomic content. Super-fine droplets may originate from alveoli regions. Bigger droplets may originate from the tracheal or bronchi rings due to mechanical friction of the exhaled gas flow with the surface covered with liquid alveolar lavage fluid. The largest droplets originate in the oral cavity and are composed of saliva. Note that these saliva droplets are the subject for filtering from the breath flow as they introduce contamination and dilution. As a consequence of this dependence on origin, the size and origin of microdroplets in exhaled breath for different breathing regimes (e.g., tidal, forced, speaking, and coughing) and humidity have been carefully studied. Sub-micron droplets tend to originate at the alveolar membrane and contain airway lining fluid (ALF). Larger droplets tend to be carried with turbulent flow from bronchial surfaces. Even larger saliva droplets tend to originate in the mouth cavity and can cause biological contamination and dilution in the sample, and should thus be avoided.

The challenge of eliminating saliva droplets can be attacked by using a physical membrane-based filter, which catches larger saliva droplets but allows smaller droplets to pass through. However, the use of such a filter can be problematic because any filter placed in the flow path of a sampling device will introduce additional pressure. When a user breathes through such a restricted flow path, the user's natural breathing pattern is changed by the additional pressure caused by the filter, which affects the metabalomic content of the sample.

Hence, what is needed is a technique for sampling human breath, which can effectively filter out saliva droplets without the drawbacks of existing filter-based techniques.

SUMMARY

The disclosed embodiments relate to a system that facilitates selective mass-size-based sorting of aerosol droplets in human breath. The system includes a mouthpiece, which is configured to receive a flow of human breath. It also includes a flow path, which is coupled to the mouthpiece. The flow path includes one or more bends, bended curves, or curves with enlarging or reducing diameters, that cause the flow of human breath to change direction, thereby causing aerosol droplets in the flow having different mass-sizes to change direction at different rates because of differences in momentum for different droplet masses, and differences in air-flow-related frictional forces for different droplet sizes. Moreover, the flow path is shaped so that droplets that change direction at different rates are directed to different destinations. The system also includes a collection path, which is coupled to the flow path so that aerosol droplets that meet a specific mass-size criterion are directed into the collection path. Finally, the system includes a condenser tube located in the collection path, wherein the condenser tube includes a cooling mechanism that cools the condenser tube to facilitate condensing aerosol droplets to sides of the condenser tube for subsequent collection.

In some embodiments, the system also includes a saliva reservoir, wherein the flow path is shaped so that larger aerosol droplets associated with saliva, which have a mass-diameter larger than a pre-specified threshold, impact walls of the flow path and accumulate in the saliva reservoir.

In some embodiments, the system includes an adjustment mechanism that selectively adjusts a mass-size threshold for filtering droplets from the aerosol flow by adjusting one or more dimensions of the flow path.

In some embodiments, the adjustment mechanism includes one or more movable baffles located in the flow path.

In some embodiments, the adjustment mechanism automatically adjusts the mass-size threshold based on a differential pressure in the flow path to ensure that the mass-size threshold remains substantially constant for different aerosol flow conditions. (This feature is particularly useful for this specific application of removing saliva droplets from human breath, and for other applications where the flow is not stable.)

In some embodiments, the flow path comprises multiple threshold-based droplet sorters connected in series, wherein each droplet sorter includes one or more bends that allow aerosol droplets having a mass-size, which is smaller or larger than a pre-specified threshold, to pass through the droplet sorter. (This sorting technique is not limited to breath and liquid droplets only. The same technique can be applied to sorting solid droplets and/or particles based on their mass and size and possibly even shape. Note that particles of different shape will have different coefficient of friction with the flow, and will thus follow the flow differently.)

In some embodiments, the collection path comprises multiple collection paths, wherein each of the multiple collection paths is configured to collect aerosol droplets that meet a different mass-size criterion. (For example, the collection pathway can be implemented as a helical pathway with multiple exits at different angular positions, wherein the diameter of the exits can also be controlled to facilitate the sorting.)

In some embodiments, each of the multiple collection paths is connected in proximity to a bend in the flow path, so that aerosol droplets have a range of turning radii, which is associated with a pre-specified range of mass-size thresholds, and are directed into the collection path.

In some embodiments, the system includes a one-way inlet valve located in the flow path in proximity to the mouthpiece, wherein the inlet valve facilitates an inhale cycle, during which air enters the flow path through the inlet valve and passes through the mouthpiece to be inhaled by a user.

In some embodiments, the system includes a one-way outlet valve installed in proximity to a distal end of the collection path, wherein the outlet valve facilitates an exhale cycle, during which the user exhales into the mouthpiece, and the exhaled breath passes through the flow path and the collection path and exits the outlet valve.

In some embodiments, the cooling mechanism comprises a thermoelectric cooling mechanism.

In some embodiments, the cooling mechanism comprises dry ice contained in a housing surrounding the condenser tube. (Note that we have performed refrigeration-cycle-based cooling as well. Refrigeration-cycle-based cooling allows temperature control down to −40 C.)

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Human Breath Sampler

Figure 1A:
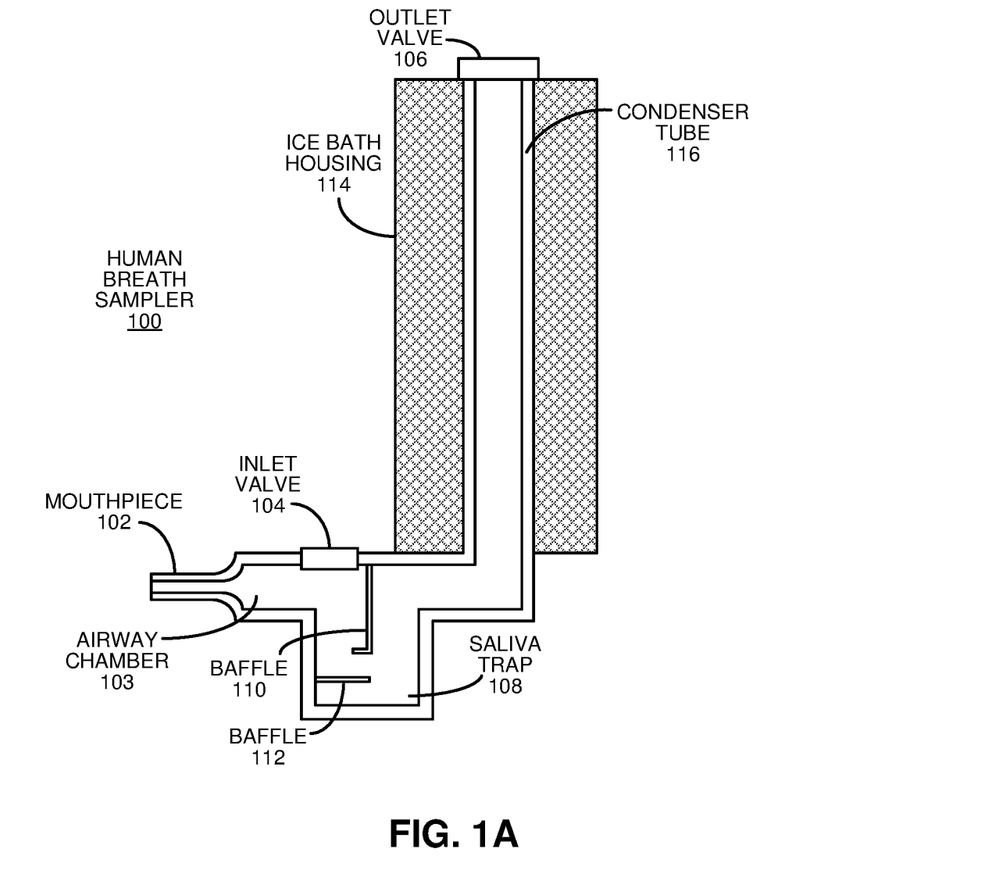
FIG. 1A illustrates an exemplary human breath sampler (HBS) in accordance with the disclosed embodiments.

FIG. 1A illustrates an exemplary human breath sampler (HBS) 100 in accordance with the disclosed embodiments. HBS 100 includes a mouthpiece 102 into which a user exhales. The exhaled breath flows into an airway chamber 103, which includes: baffles 110 and 112, a saliva trap 108 and a distal condenser tube 116. Condenser tube 116 includes a cooling mechanism comprising a surrounding insulated ice bath housing 114, which is filled with dry ice. Instead of using dry ice, condenser tube 116 can alternatively be cooled using an array of thermoelectric plates or gas-refrigeration-based system.

Figure 1B:
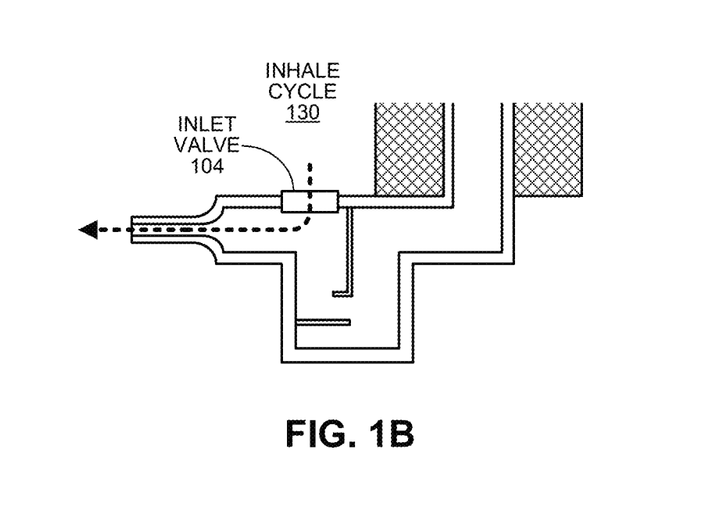
FIG. 1B illustrates an inhale cycle for an HBS in accordance with the disclosed embodiments.
Figure 1C:
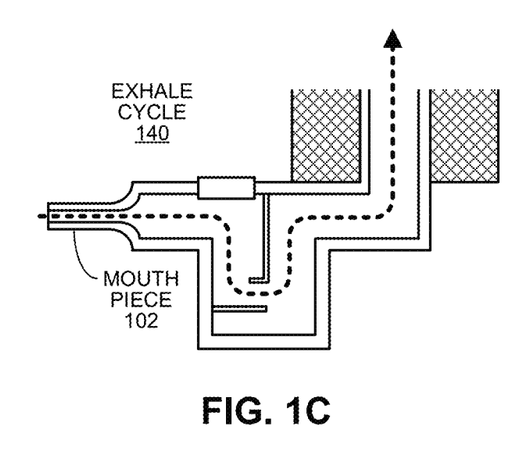
FIG. 1C illustrates an exhale cycle for an HBS in accordance with the disclosed embodiments.

Airway chamber 103 is equipped with a pair of one-way valves, including an inlet valve 104 and an outlet valve 106, which can be implemented using silicone flap valves. (However, note that in general any type flexible flap material or any type of actuated valve can be used.) Inlet valve 104 is installed in the HBS housing in proximity to mouthpiece 102 and in front of saliva trap 108. In contrast, outlet valve 106 is installed at the outlet of the condenser tube 116. Inlet valve 104 and outlet valve 106 are designed to promote unidirectional breath flow and to keep condenser tube 116 closed during inhale cycles to prevent condensation from the ambient air from entering condenser tube 116. FIG. 1B illustrates an inhale cycle 130, during which air enters airway chamber 103 through the inlet valve 104 and passes through mouthpiece 102 to be inhaled by a user. FIG. 1C illustrates an exhale cycle 140, during which the user exhales into mouthpiece 102, and the exhaled breath passes through airway chamber 103 and condenser tube 116 before exiting through outlet valve 106. During operation, the inlet valve 104 and outlet valve 106 operate collectively to allow only exhaled breath to pass through condenser tube 116, which prevents users from experiencing extreme temperature differences in inhaled air. Hence, inlet valve 104 and outlet valve 106 provide sufficient, pressure-drop-free airflow during inspiration and expiration operations.

Note that chemically inert materials are used for the portions of HBS that come into contact with breath to reduce any chemical absorbance and carry over effects among users. Moreover, the HBS can be sanitized and reused; the only disposable parts include: a removable mouthpiece adapter, which is part of mouthpiece 102; and a disposable inlet valve 104.

The aerodynamic flows within HBS 100 are designed to achieve minimum pressure resistance and an efficient condensation rate; and to provide a mechanism for filtering saliva droplets from the exhaled breath flow. Note that the saliva trap 108 of the device provides an airflow path, which is designed to facilitate passage of droplets having a mass-diameter smaller than a pre-defined threshold. Any droplet above this threshold is eliminated from the breath flow and is collected in saliva trap 108. Note that the threshold size for the droplets can be adjusted by moving the position of vertical baffle 110. Also note that no physical filtering element is used in HBS 100 because such a filtering element can adversely affect the gathered samples by eliminating useful compounds from the exhaled breath.

Figure 1D:
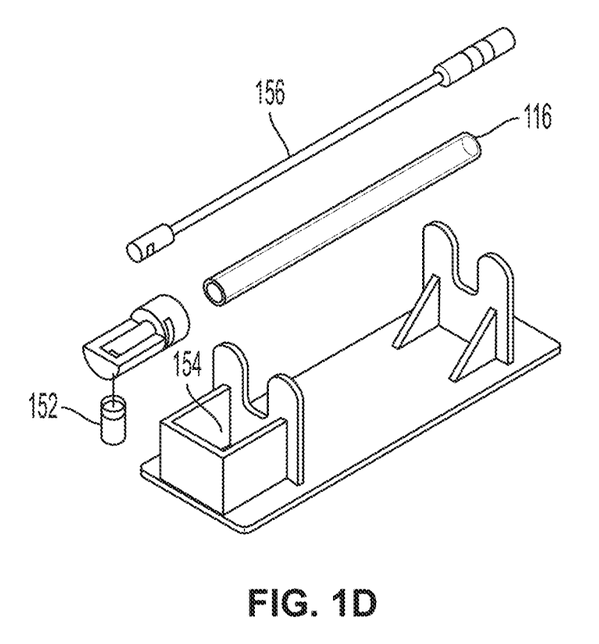
FIG. 1D illustrates a retrieval press for an HBS in accordance with the disclosed embodiments.

Sample transfers are efficient and quick, so that the sample does not undergo a physical phase change from ice into liquid, which is crucial for metabolomic content preservation. Hence, to retrieve the collected sample from condenser tube 116 into a vial 152, the dry ice pellets are first removed from insulated ice bath housing 114. Condenser tube 116 is then placed into a sample retrieval press 154 as is illustrated in FIG. 1D. The frozen EBC sample is then removed from the inner lumen side of condenser tube 116 with a polytetrafluoroethylene (PTFE) plunger 156. During this process, two sharp notches on the front end of the plunger 156, similar to an end mill tool, clear the ice out with a rotational movement. Also, two PTFE gaskets in the middle part of plunger 156 are slightly larger than the plunger body and act to scribe remaining sample from the tube walls.

Breath Flow, Heat Exchange, and Saliva Filtering

The flow regime, pressure resistance, heat transfer, and condensation rate for HBS 100 can be estimated using both analytical and numerical techniques. The pressure drop in the condenser tube can be estimated with the Darcy friction factor and known fluid properties in accordance with the following equation $$\Delta p = \rho g \left( \frac{fLV^2}{2dg} + \Delta z \right) \quad \text{Eq. 1}$$

where $\rho$ is the fluid density, g is the acceleration of gravity, f is the Darcy friction factor, V is the flow velocity, and d is the tube inner diameter. Note that the change due to gravity $\Delta z$ is equal to the glass tube length, L, because the tube operates in a vertical position.

The temperature at the outlet of the device can be evaluated with the average convection heat transfer coefficient $\bar{h}$ assuming a constant surface temperature $T_s$ and a negligible pressure gradient to treat the fluid as incompressible as is expressed in the following equation $$\frac{T_s - T_o}{T_s - T_i} = \exp\left(-\frac{PL\bar{h}}{\dot{m}C_p}\right) \quad \text{Eq. 2}$$

where, $T_i$ is the inlet temperature, P is the tube inner perimeter, $\dot{m}$ is the mass flow rate, and $C_p$ is the specific heat. Corresponding fluid properties at the outlet of the device are evaluated at this estimated temperature, $T_o$. The constant-surface-temperature assumption can be validated by comparing an estimation of the heat that can be conducted through the glass tube wall to the heat absorbed from the fluid during condensation, freezing, and cooling. Under the most conservative conditions, assuming a minimum temperature difference and a highest breath flow rate, the possible amount of heat conducted through the glass wall exceeds the amount of heat released by warm breath.

The rate of heat transfer $\dot{Q}$ between the moist breath stream and the chilled surface of the condenser tube is evaluated with mass and energy rate balances. The mass of the air is preserved, while water vapor partially condenses. Assuming steady state and saturated fluid properties at the inlet and outlet temperatures, we can evaluate the condensation rate through the following equation $$\dot{Q}_{cv} = \dot{m}_a[h_{a_o} - h_{a_i} + \omega_o h_{g_o} - \omega_i h_{g_i} + (\omega_i - \omega_o)h_{f_o}] \quad \text{Eq. 3}$$

where $\dot{m}_a$ is the mass flow rate of dry air, $h_a$ is the specific enthalpy of dry air, $h_g$ is the specific enthalpy of water vapor, $h_f$ is the specific enthalpy of the condensate, and $\omega$ is the humidity ratio at the inlet and outlet.

The above-described analytical results for pressure, resistance and heat exchange in the device were confirmed with a numerical simulation of a non-isothermal flow using the COMSOL Multiphysics® Simulation Software. The geometrical scale of the model was set to 1:1, which corresponds to the actual dimensions of the device. During the simulations, the inlet flow rate was set to correspond to an average tidal breathing rate of 12-20 breaths/minute, with a tidal volume of 0.5 L exhaled in 1 second. The fluid properties at the inlet were approximated with those of saturated air mixture at body core temperature, wherein the surface temperature of the condenser corresponded to the experimentally measured value (−30° C.). The numerical solution was performed in three steps. First, velocity and pressure distributions in the device were evaluated assuming steady state flow. The heat exchange between breath and condenser surface was evaluated using two models: a first model wherein heat transfer in the fluids was determined based on the previously estimated fluid velocity field; and a second model that simulated a non-isothermal fluid flow in the device. The droplet flight paths inside the saliva filter were estimated using a particle-tracing application in COMSOL®. Finally, the dimensions of the saliva trap geometries (baffle length and position) were chosen based on the numerical solution results.

Flow Optimization and Aerodynamic Saliva Droplets Filtering

Figure 2A:
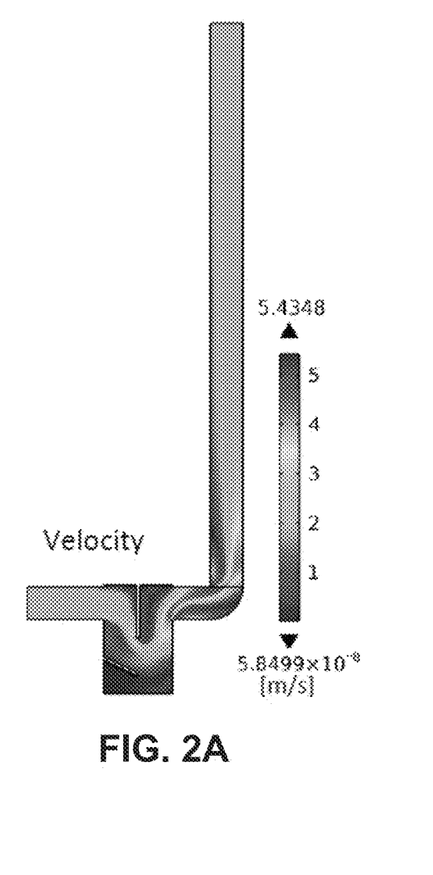
FIG. 2A presents a diagram illustrating a simulated velocity profile for an HBS in accordance with the disclosed embodiments.
Figure 2B:
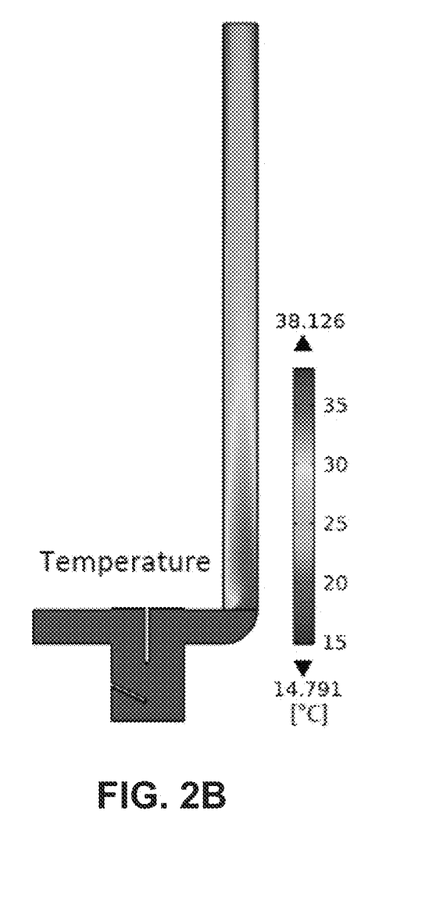
FIG. 2B presents a diagram illustrating a simulated temperature profile for an HBS in accordance with the disclosed embodiments.

Low airflow backpressure and high condensation rate are two desirable characteristics for a breath sampler. The backpressure can be a significant problem for breath samplers because high backpressures can cause a deviation from normal respiration patterns that can affect the metabolomic content of breath. Human respiratory devices are rated at or below a 100 Pa pressure drop for an average adult human By approximating an average tidal respiratory rate of 20 breaths/minute with a tidal volume of 0.5 L exhaled in 1 second as a constant flow rate 0.5 L/s, we can estimate the backpressure and temperature drop in the device. FIGS. 2A and 2B show numerical simulation results for velocity and temperature, respectively, of a non-isothermal laminar flow within the HBS using the COMSOL® software. Both types of solutions, numerical and analytical, closely agree on pressure resistance and temperature drop in the device. The corresponding pressure drop is 31.53 and 38.13 Pa estimated with analytical Eq. (1) and corresponding numerical simulations, respectively. The estimated temperature of the fluid at the outlet is 24.42° C. and 25° C. based on analytical Eq. (2) and numerical simulations, respectively.

The condensation rate, which is estimated from the mass-and-energy-balance Eq. (3) based on the difference of saturated fluid properties at an inlet temperature of 36.6° C. and an estimated fluid temperature at the outlet of 25° C., is 10.5 mg/s. The total theoretical condensed EBC volume is 2.1 g assuming that condensation occurs only during exhalation maneuvers: 200 seconds (10 min sampling, 20 breaths/min, flow rate 0.5 L/s during exhalation).

Figure 2C:
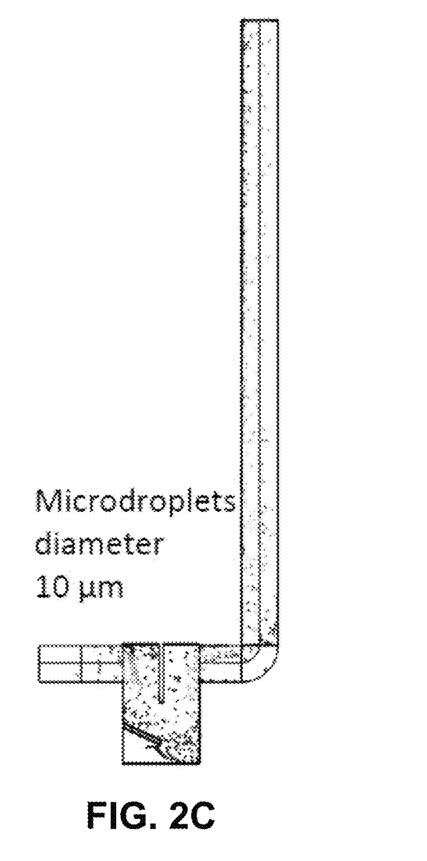
FIG. 2C presents a diagram illustrating simulated trajectories of particles with a mass-size below a threshold for an HBS in accordance with the disclosed embodiments.
Figure 2D:
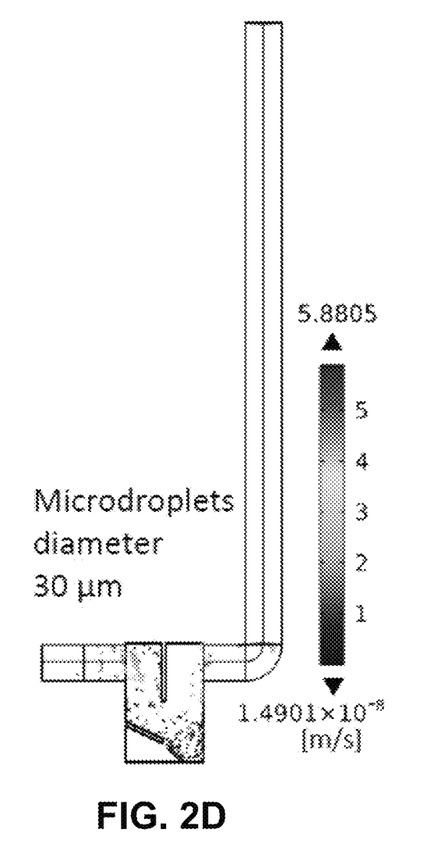
FIG. 2D presents a diagram illustrating simulated trajectories of particles with a mass-size above a threshold for an HBS in accordance with the disclosed embodiments.

FIGS. 2C and 2D illustrate results of numerical simulations for the passage of the microdroplets through the saliva trap. The size of the microdroplets filtered from the breath flow in the saliva trap was estimated using a particle-tracking mode of the COMSOL® software. Exhaled droplets with a diameter less than 20 μm are predicted to pass with the breath flow as illustrated in FIG. 2C. In contrast, exhaled droplets with diameter greater than 20 μm are predicted to deviate from the flow and pass into the saliva trap as illustrated in FIG. 2D. Although a more computationally accurate solution would resolve additional details about the design of the saliva filter, this solution generally validates the design concept. The ability of the filter to reduce the amount of saliva was also confirmed with the experimental measurements of an amylase level present in the collected EBC samples. A benefit of this design is that it facilitates selective filtering of microdroplets by capturing heavy saliva droplets, while allowing passage of small droplets that originate from deep in the lungs that contain meaningful metabolites for health diagnostics.

A major benefit of this HBS device is the significantly large captured fraction of the metabolomic content from exhaled breath. Note that the physical phase of the EBC sample (solid versus liquid) and the fraction of the captured VOCs depend on the condensation temperature and its stability during all collection steps. This hardware design is optimized to facilitate quick sample transfer to avoid sample contamination and a physical phase change. Note that a thick glass tube (4 mm wall) provides a thermal mass to keep the EBC sample frozen during the sample-retrieval process, which can be completed in 1-2 minutes. Also note that the collected EBC samples can be transferred into storage vials in their original solid phase.

Hence, the above-described aerodynamic saliva-filtering technique not only eliminates large saliva droplets from the breath flow, but also performs selective mass filtering of the microdroplets having mass-sizes above a pre-specified threshold. This saliva trap design is based on the ability of each droplet to trace the flow. The behavior of a droplet suspended in a fluid flow is characterized with the Stokes number, which is defined as the ratio of the characteristic time of a particle (time required to change particle flight direction) to the characteristic time of the flow (time required for fluid flow to change its direction) around an obstacle. A small droplet with a low Stokes number follows the fluid flow closely, because its momentum is immediately affected by the change in fluid velocity; the droplet's momentum changes as fast as the fluid flow. In contrast, a larger, heavier droplet has a larger momentum and requires more time to change its direction in response to a change in the flow velocity field. Provided that droplets with different masses are propagating in the same fluid flow, they all have the same time interval for their direction change to follow the fluid flow around an obstacle, but require different amounts of time for that change to occur. Thus, larger droplets will fail to follow the fluid flow around an obstacle because they need more time to change their direction than it takes the fluid to change direction, and will consequently follow their own straighter path, which will prevent them from propagating along with the fluid flow around an obstacle. Note that this ability of a droplet to follow the fluid flow is not solely determined by its mass and size but also by the flow regime (turbulent or laminar) and fluid properties (density, viscosity). This dependence is described by the Reynolds number and associated drag coefficient.

Process of Operation

Figure 3:
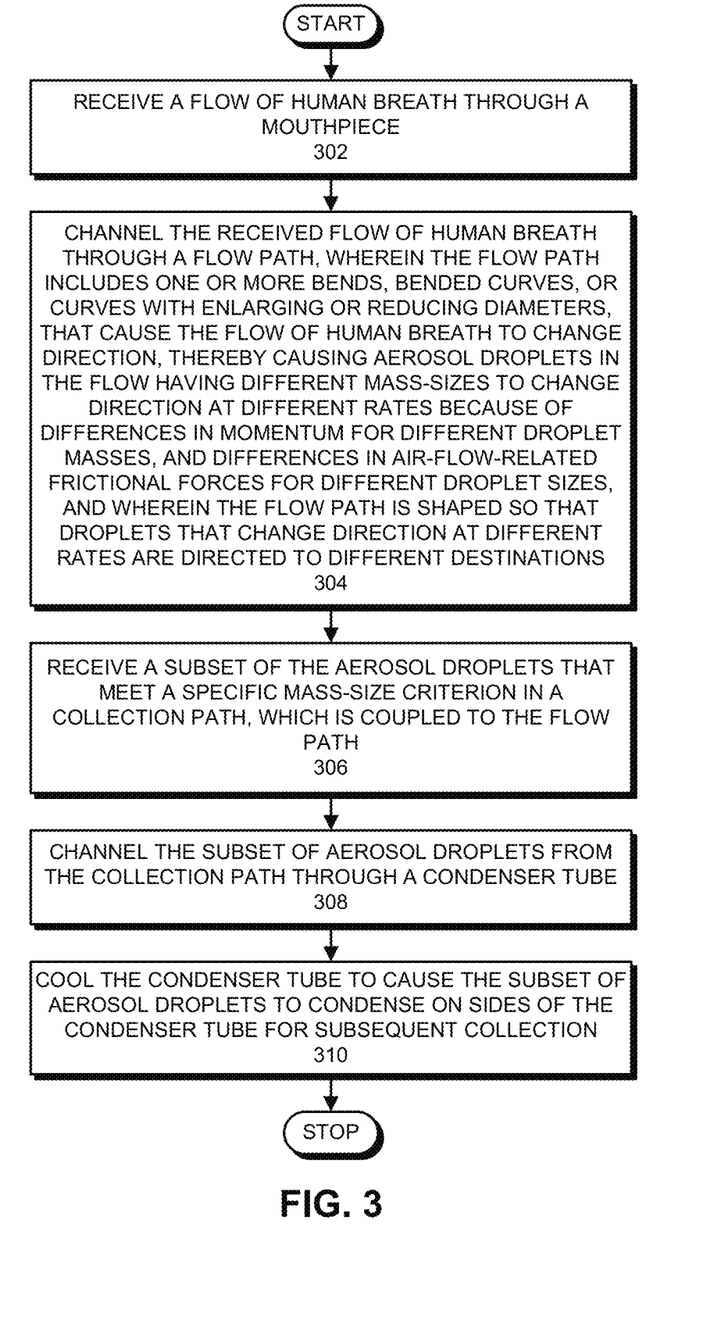
FIG. 3 presents a flow chart illustrating the process of operating an HBS, which selectively sorts aerosol droplets in human breath based on their mass-size in accordance with the disclosed embodiments.

FIG. 3 presents a flow chart illustrating the process of operating a human breath sampler, which selectively sorts aerosol droplets in human breath based on mass-size in accordance with the disclosed embodiments. First, the system receives a flow of human breath through a mouthpiece (step 302). Next, the system channels the received flow of human breath through a flow path, wherein the flow path includes one or more bends, bended curves, or curves with enlarging or reducing diameters, that cause the flow of human breath to change direction, thereby causing aerosol droplets in the flow having different mass-sizes to change direction at different rates because of differences in momentum for different droplet masses, and differences in air-flow-related frictional forces for different droplet sizes, and wherein the flow path is shaped so that droplets that change direction at different rates are directed to different destinations (step 304). (Note that the bends are not limited to be 90° or 180°.) The system subsequently receives a subset of the aerosol droplets that meet a specific mass-size criterion in a collection path, which is coupled to the flow path (step 306). The system then channels the subset of aerosol droplets from the collection path through a condenser tube (step 308). Note that the system cools the condenser tube to cause the subset of aerosol droplets to condense on sides of the condenser tube for subsequent collection (step 310).

Miniature HBS

Figure 4A:
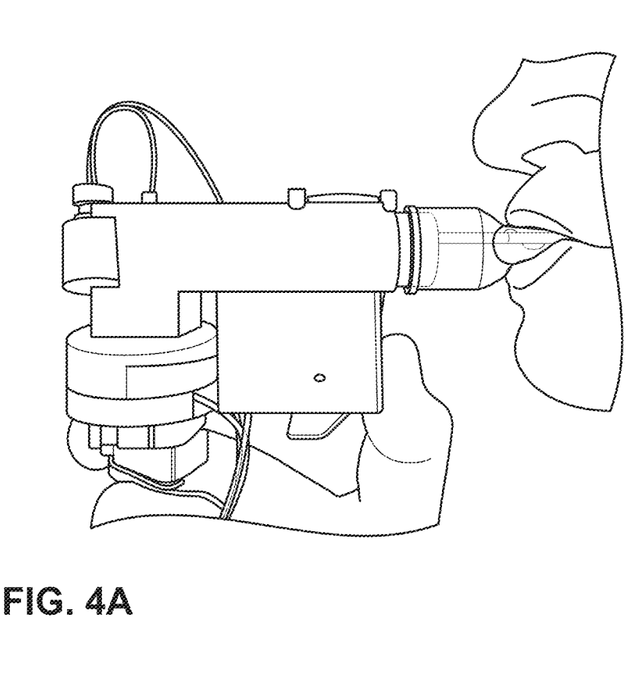
FIG. 4A illustrates a miniature HBS and an associated condenser element in accordance with the disclosed embodiments.
Figure 4B:
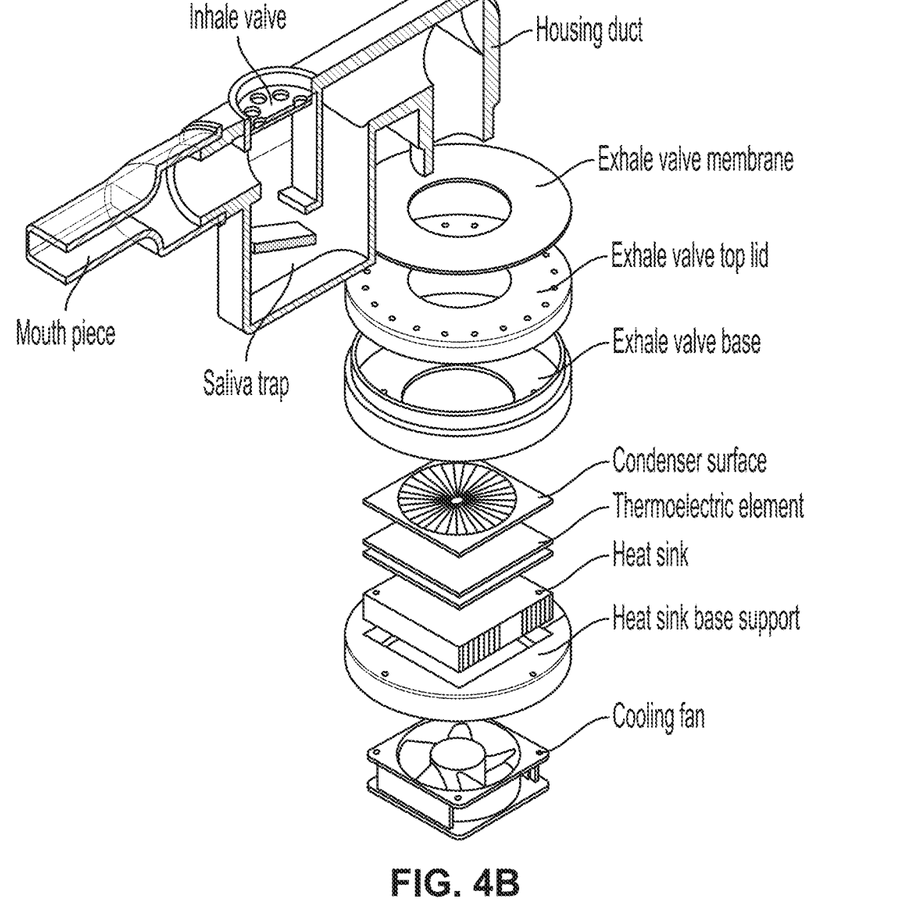
FIG. 4B illustrates various components that comprise the miniature HBS in accordance with the disclosed embodiments.
Figure 4C:
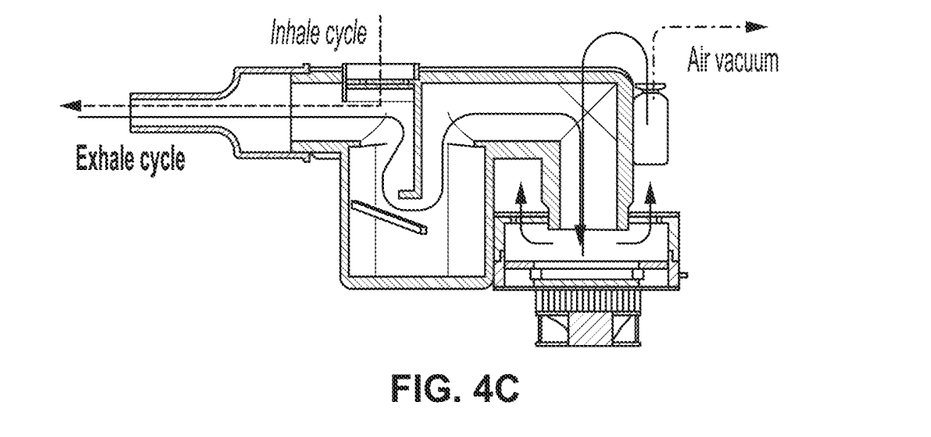
FIG. 4C illustrates presents a cutaway view of the miniature HBS in accordance with the disclosed embodiments.

The above-described HBS can also be miniaturized by replacing the condenser tube at the outlet end with a small (35×35 mm) hydrophobic self-cleaning condenser surface, which is cooled with a thermoelectric element. The mouthpiece and saliva-filtering components can remain the same. This embodiment is illustrated in FIGS. 4A-4C. The left side of FIG. 4A presents a photograph of the hydrophobic self-cleaning condenser surface, while the right side of FIG. 4A illustrates the miniaturized HBS being used to collect a breath sample. FIG. 4B illustrates various components that comprise the miniature HBS, while FIG. 4C presents a cutaway view of the miniature HBS that illustrates airflow through the miniature HBS.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. An apparatus that facilitates selective mass-size-based sorting of aerosol droplets in human breath, comprising:
   an input configured to receive a flow of human breath;
   an airway chamber coupled to the input and enclosed by a first housing composed of two or more horizontal sections and two or more vertical sections;
   wherein the airway chamber is shaped with two or more bends, wherein a first bend positioned closest to the input among the two or more bends is formed by a first vertical section of the first housing and a vertical baffle positioned in the airway chamber and attached to a first horizontal section of the first housing, wherein the first bend causes the flow of human breath to move in a downward direction, wherein a second bend following the first bend is formed by the first vertical section of the first housing and a horizontal baffle attached to the first vertical section of the first housing, wherein the horizontal baffle is positioned above a saliva trap located at a bottom section of the first housing and is movable to adjust its position, wherein the second bend causes the flow of human breath to change direction from the downward direction to a horizontal direction and to move above the horizontal baffle, wherein the two or more bends cause the flow of human breath to change directions multiple times, thereby causing aerosol droplets in the flow having different mass-sizes to change direction at different rates as a result of differences in momentum for different masses of the aerosol droplets, and differences in air-flow-related frictional forces for different sizes of the aerosol droplets, and wherein the airway chamber is shaped so that the aerosol droplets that change direction at different rates are directed to different destinations;
   a collection path coupled to the airway chamber so that aerosol droplets that meet a specific mass-size criterion are directed into the collection path; and
   a condenser tube in the collection path, wherein the condenser tube includes a cooling mechanism that cools the condenser tube to facilitate condensing aerosol droplets to sides of the condenser tube for subsequent collection.

2. The apparatus of claim 1,
   wherein the airway chamber is shaped so that larger aerosol droplets associated with saliva, which have a mass-diameter larger than a pre-specified threshold, impact walls of the airway chamber and accumulate in the saliva trap.

3. The apparatus of claim 1, further comprising an adjustment mechanism that selectively adjusts a mass-size threshold for filtering droplets from the aerosol flow by adjusting one or more dimensions of the airway chamber.

4. The apparatus of claim 3, wherein the adjustment mechanism includes one or more movable baffles located in the airway chamber.

5. The apparatus of claim 3, wherein the adjustment mechanism automatically adjusts the mass-size threshold based on a differential pressure in the airway chamber to ensure that the mass-size threshold remains substantially constant for different aerosol flow conditions.

6. The apparatus of claim 1, wherein the airway chamber comprises multiple threshold-based droplet sorters connected in series, wherein each droplet sorter includes one or more bends that allow aerosol droplets having a mass-size, which is smaller or larger than a pre-specified threshold, to pass through the droplet sorter.

7. The apparatus of claim 1, further comprising:
   a one-way inlet valve located in the airway chamber in proximity to the input, wherein the inlet valve facilitates an inhale cycle, during which air enters the airway chamber through the inlet valve and passes through the input to be inhaled by a user; and
   a one-way outlet valve installed in proximity to a distal end of the collection path, wherein the outlet valve facilitates an exhale cycle, during which the user exhales into the input, and the exhaled breath passes through the airway chamber and the collection path and exits the outlet valve.

8. The apparatus of claim 1, wherein the cooling mechanism comprises a thermoelectric cooling mechanism.

9. The apparatus of claim 1, wherein the cooling mechanism comprises dry ice contained in a housing surrounding the condenser tube.

10. A method for selectively sorting aerosol droplets in human breath based on mass-size, comprising:
    receiving a flow of human breath through an input;
    channeling the received flow of human breath through an airway chamber that is enclosed by a first housing composed of two or more horizontal sections and two or more vertical sections, wherein the airway chamber is shaped with two or more bends, wherein a first bend positioned closest to the input among the two or more bends is formed by a first vertical section of the first housing and a vertical baffle positioned in the airway chamber and attached to a first horizontal section of the first housing, wherein the first bend causes the flow of human breath to move in a downward direction, wherein a second bend following the first bend is formed by the first vertical section of the first housing and a horizontal baffle attached to the first vertical section of the first housing, wherein the horizontal baffle is positioned above a saliva trap located at a bottom section of the first housing and is movable to adjust its position, wherein the second bend causes the flow of human breath to change direction from the downward direction to a horizontal direction and to move above the horizontal baffle, wherein the two or more bends cause the flow of human breath to change directions multiple times, thereby causing aerosol droplets in the flow having different mass-sizes to change direction at different rates as a result of differences in momentum for different masses of the aerosol droplets, and differences in air-flow-related frictional forces for different sizes of the aerosol droplets, and wherein the airway chamber is shaped so that the aerosol droplets that change direction at different rates are directed to different destinations;

receiving a subset of the aerosol droplets that meet a specific mass-size criterion in a collection path, which is coupled to the airway chamber;

channeling the subset of aerosol droplets from the collection path through a condenser tube; and cooling the condenser tube to cause the subset of aerosol droplets to condense on sides of the condenser tube for subsequent collection.

11. The method of claim 10, wherein the airway chamber is shaped so that larger aerosol droplets associated with saliva, which have a mass-diameter larger than a pre-specified threshold, impact walls of the airway chamber and accumulate in the saliva trap.

12. The method of claim 10, further comprising selectively adjusting a mass-size threshold for filtering droplets from the aerosol flow by adjusting one or more dimensions of the airway chamber.

13. The method of claim 12, wherein adjusting the mass-size threshold comprises adjusting one or more movable baffles located in the airway chamber.

14. The method of claim 12, wherein adjusting the mass-size threshold comprises automatically adjusting the mass-size threshold based on a differential pressure in the airway chamber to ensure that the mass-size threshold remains substantially constant for different aerosol flow conditions.

15. The method of claim 10, wherein the airway chamber comprises multiple threshold-based droplet sorters connected in series, wherein each droplet sorter includes one or more bends that allow aerosol droplets having a mass-size, which is smaller or larger than a pre-specified threshold, to pass through the droplet sorter.

16. The method of claim 12, further comprising:

using a one-way inlet valve, which is located in the airway chamber in proximity to the input, to facilitate an inhale cycle, during which air enters the airway chamber through the inlet valve and passes through the input to be inhaled by a user; and using a one-way outlet valve, which is installed in proximity to a distal end of the collection path, to facilitate an exhale cycle, during which the user exhales into the input, and the exhaled breath passes through the airway chamber and the collection path and exits the outlet valve.

17. The method of claim 10, wherein cooling the condenser tube comprises using a thermoelectric cooling mechanism to cool the condenser tube.

18. The method of claim 10, wherein cooling the condenser tube comprises using dry ice contained in a housing surrounding the condenser tube to cool the condenser tube.

* * * * *

UNITED STATES PATENT AND TRADEMARK OFFICE
CERTIFICATE OF CORRECTION

| | | |
|---|---|---|
| PATENT NO. | : 11,813,050 B2 | Page 1 of 1 |
| APPLICATION NO. | : 16/347560 | |
| DATED | : November 14, 2023 | |
| INVENTOR(S) | : Cristina E. Davis et al. | |

It is certified that error appears in the above-identified patent and that said Letters Patent is hereby corrected as shown below:

In the Specification (At Column 1, Line 15) please insert the paragraph:
-- GOVERNMENT LICENSE RIGHTS
This invention was made with government support under TR000002 awarded by the National Institutes of Health, and N00014-13-1-0580 awarded by the Office of Naval Research. The government has certain rights in the invention. --

Signed and Sealed this
First Day of April, 2025

Coke Morgan Stewart
*Acting Director of the United States Patent and Trademark Office*